United States Patent [19]

Schelbeck

[11] Plant 5,162

[45] Dec. 20, 1983

[54] BEGONIA PLANT NAMED DORTHE

[75] Inventor: Erland V. Schelbeck, Odense, Denmark

[73] Assignee: L. Daehnfeldt Ltd., Odense, Denmark

[21] Appl. No.: 420,521

[22] Filed: Sep. 20, 1982

[51] Int. Cl.[3] ..... A01H 5/00

[52] U.S. Cl. ..... Plt./68

[58] Field of Search ..... Plt./68

*Primary Examiner*—Robert E. Bagwill

*Attorney, Agent, or Firm*—Schwartz, Jeffery, Schwaab, Mack, Blumenthal & Koch

[57] ABSTRACT

A begonia plant named Dorthe having double deep bright red sterile flowers, medium size firm waxy foliage, upright growth easily controlled for plant height, outstanding keeping qualities, and being capable of flowering in all seasons for commercial purposes.

1 Drawing Figure

1

The present invention relates to a new and distinctive cultivar of begonia plant, botanically known as hiemalis begonia (Fotsch), and known by the cultivar name Dorthe.

The new cultivar was discovered by me as a seedling from a controlled crossing of seedling P-238 as the seed parent with Socotrana as the pollen parent. Asexual reproduction by stem and leaf cuttings has reproduced the unique features of the new cultivar through successive propagations.

The following characteristics distinguish the new begonia from both its parents and other begonias commercially known and used in the floriculture industry:

1. My seedling has smaller leaves, more compact growth habit, and year round flowering when compared to the tuberous seed parent P-238, which drops its flowers during the winter months.

2. The foliage of my new seedling is darker green with red pigmentation in comparison to the light green foliage of the pollen parent Socotrana. The flowers are double red while Socotrana flowers are single and light pink. In comparison to my cultivar Connie, disclosed in my pending application Ser. No. 420,500, filed 9/20/82, Dorthe's flowers are true red whereas the flowers of Connie have a tint of blue giving the flowers a rose-red coloration. Foliage of Connie is lighter than Dorthe.

3. In comparison to Riegers Cultivar Nixe (U.S. Plant Pat. No. 3,967), Dorthe has larger deeper red double flowers. The foliage of Dorthe is about the same size as foliage of Nixe, but is flat and more circular.

4. The other red double flowering hiemalis begonia that can be compared is Claudia (unpatented), a red mutation of Aphrodite Cherry Red. My new cultivar is more upright, flowers are brighter red and remain on the plant during low light periods.

5. Propagation by leaf cuttings is uniform, producing 3–4 adventious shoots during all seasons.

6. Flowering response is uniform in all seasons, providing day length for flower imitation is no more than 11 hours per day.

7. The flower keeping quality is very good in all seasons. However, as with most dark red flowering begonias, the flowers will sun scald if subjected to high light.

8. The foliage is dark, waxy green with red infusion giving an excellent contrast to the bright red double flowers.

9. Dorthe responds to applications of Cycocel or A-Rest for maintaining a short compact plant. The

2 illustrated plant had one application of A-Rest 3 weeks after the start of flower initiation.

10. The excellent keeping qualities allow Dorthe to be used for hanging baskets for interior decorating at all seasons, whereas Riegers Aphrodite types drop their flowers in winter.

The accompanying colored photograph taken June 1982 illustrates in perspective the overall appearance of Dorthe grown in a 15 cm. plastic pot and showing the colors as true as it is reasonably possible to obtain in a colored reproduction of this type.

The following is a detailed description of my new begonia cultivar based on plants produced under commercial practices in Odense, Denmark, and Ashtabula, Ohio. Color references are made to The Royal Horticultural Society Colour Chart except where general terms of ordinary dictionary significance are used.

Parentage: Tuberous seedling p-238 crossed with b. Socotrana.

Propagation:

(a) *Type cutting.*—Leaf cutting.

(B) *Time to root.*—18 days at 21° C. summer; 28 days at 21° C. winter.

(C) *Rooting habit.*—Uniform dendritic, fibrous.

(D) *Time for shoot development.*—to 5–6 cm. in length, approximately 70 days in summer and up to 85 days in winter.

Plant description:

(A) *Form.*—Compact, close internodes, semi-rigid appearance of stems with first flower clusters being tight to foliage, becoming semi-pendulous at maturity; herbaceous.

(B) *Habit of growth.*—Cultivar has above average branching habits, tends to be upright but easily controlled by growth regulators or pinching and other types of plant management for shortening stem length.

(C) *Flower bud description.*—Buds are circular, flat, up to 2 cm.; dark pink to red as tepals open.

(D) *Flowers borne.*—Initially on a sturdy raceme, but eventually becoming somewhat pendulous at maturity; backside of flower flat, top round and mounded.

(E) *Quantity.*—Each raceme initially may have 6–8 flowers in blossom at one time. Additional flowers will continue to develop as the mature flowers drop away from sepals. Flowers are double to compound.

(F) *Tepals.*—(1) Shape; nearly round. (2) Color top side in winter when opening, between red 44B and red 43A, fading to approximately 43B; underside approximately 43B. (3) Number of tepals: Varying normally from 42–48, although in one instance 54 were present. (4) Size of tepals: Basal tepals 3 cm. in diameter; internal tepals 1–1.5 cm. (5) Flower size: Up to 5 cm.

(G) *Reproductive organs.*—Cultivar is a sterile triploid.

Disease reistance: Has above average resistance to powdery mildew.

I claim:

1. A new and distinct cultivar of begonia named Dorthe, as described and illustrated, and particularly characterized by its compact and upright growth habit; year round flowering; large deep red double flowers; medium and firm waxy foliage, and by its outstanding keeping qualities.

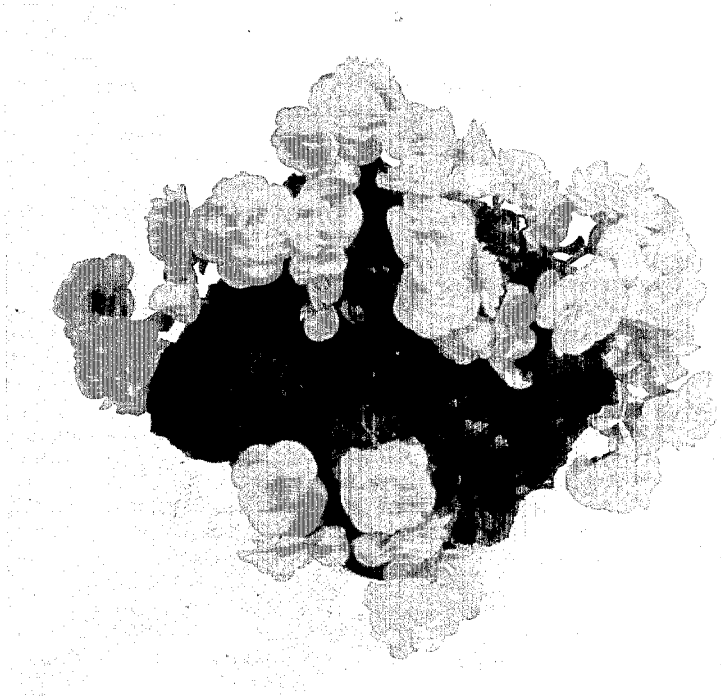

* * * * *